(12) United States Patent
Amron

(10) Patent No.: US 9,717,574 B2
(45) Date of Patent: Aug. 1, 2017

(54) DISPOSABLE DENTAL FLOSS SEGMENT WITH ROLLED PAPER HANDLE ENDS

(71) Applicant: Scott Amron, Smithtown, NY (US)

(72) Inventor: Scott Amron, Smithtown, NY (US)

( * ) Notice: Subject to any disclaimer, the term of this patent is extended or adjusted under 35 U.S.C. 154(b) by 0 days.

(21) Appl. No.: 13/986,738

(22) Filed: Sep. 3, 2013

(65) Prior Publication Data

US 2015/0297326 A1 Oct. 22, 2015

Related U.S. Application Data

(60) Provisional application No. 61/689,156, filed on May 30, 2012.

(51) Int. Cl.
*A61C 15/00* (2006.01)
*A61C 15/04* (2006.01)

(52) U.S. Cl.
CPC .......... *A61C 15/046* (2013.01); *A61C 15/043* (2013.01)

(58) Field of Classification Search
CPC ......... A61C 15/00; A61C 15/02; A61C 15/04; A61C 15/041; A61C 15/043; A61C 15/045; A61C 15/046
USPC ....... 132/323, 200, 321, 324, 326, 327, 328, 132/329
See application file for complete search history.

(56) References Cited

U.S. PATENT DOCUMENTS

| | | | | |
|---|---|---|---|---|
| 3,802,445 A | * | 4/1974 | Wesley | A61C 15/043 132/321 |
| 3,913,596 A | * | 10/1975 | Stuart | A61C 15/02 132/321 |
| 4,050,470 A | * | 9/1977 | Miller | A61C 15/046 132/323 |
| 4,403,625 A | * | 9/1983 | Sanders | A61C 15/046 132/323 |
| 4,519,408 A | * | 5/1985 | Charatan | A61C 15/043 132/321 |
| 4,579,221 A | * | 4/1986 | Corella | A61C 15/043 206/388 |
| 4,712,572 A | * | 12/1987 | Hovel, III | A61C 15/043 132/321 |
| 4,852,728 A | * | 8/1989 | Court | A61C 15/043 132/321 |
| 4,986,289 A | * | 1/1991 | McWhorter | A61C 15/043 132/323 |
| 5,174,314 A | * | 12/1992 | Charatan | A61C 15/043 132/321 |
| 5,224,501 A | * | 7/1993 | McKenzie | A61C 15/046 132/321 |
| 5,560,379 A | * | 10/1996 | Pieczenik | A61C 15/02 132/329 |
| 5,564,446 A | * | 10/1996 | Wiltshire | A45D 44/18 132/309 |
| 5,582,194 A | * | 12/1996 | Dolan | A61C 15/043 132/321 |
| 5,911,229 A | * | 6/1999 | Chodorow | A61C 15/046 132/321 |
| 6,019,109 A | * | 2/2000 | Moore | A61C 15/046 132/323 |

(Continued)

*Primary Examiner* — Rachel Steitz

(57) ABSTRACT

A disposable dental flossing device is provided for improved handling, comprised of a floss segment with two tightly rolled paper handles at each end. The floss runs the entire length of the device and is anchored at each end by cutting and heating the floss. A section of exposed floss separates the two handles.

10 Claims, 7 Drawing Sheets

(56) References Cited

U.S. PATENT DOCUMENTS

| | | | | |
|---|---|---|---|---|
| 6,234,182 B1* | 5/2001 | Berglund | ............ | A61C 15/046 132/323 |
| 7,146,987 B2* | 12/2006 | Tse | ............ | A61C 15/046 132/323 |
| 7,819,126 B2* | 10/2010 | Bush | ............ | A61C 15/043 132/323 |
| 8,127,778 B1* | 3/2012 | David | ............ | A61C 15/043 132/321 |
| 2006/0070636 A1* | 4/2006 | Peters, Jr. | ............ | A61C 15/02 132/324 |
| 2010/0018547 A1* | 1/2010 | Roemuss | ............ | A61B 17/244 132/323 |
| 2011/0265811 A1* | 11/2011 | Lorch | ............ | A61C 15/041 132/323 |

* cited by examiner

Fig 3a Fig 3b
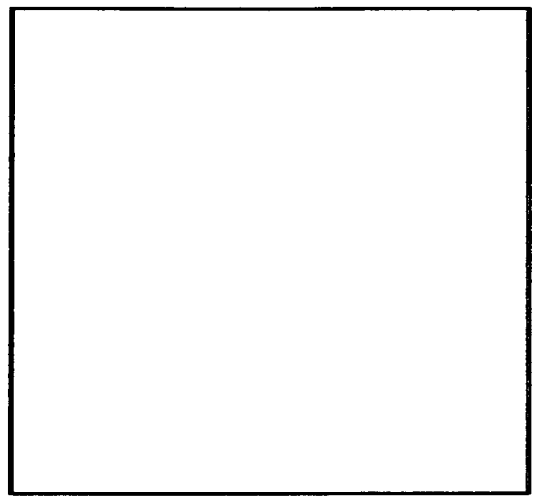
Fig 4a
Fig 4b
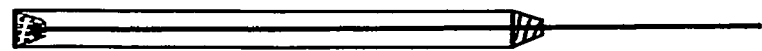

DISPOSABLE DENTAL FLOSS SEGMENT WITH ROLLED PAPER HANDLE ENDS

FIELD OF THE INVENTION

The present invention claims the benefit of the earlier Provisional Patent Application No. 61/689,156 of the same name filed on May 30, 2012 and relates to the field of dental hygiene and more specifically to a disposable flossing device with improved handling.

BACKGROUND OF THE INVENTION

Background

Current dental floss on-a-roll flossing solutions comprise a plastic case, a plastic insert, a plastic roll on which the floss is wound and a metal cutter. Excess floss is wasted when wrapped around the fingers of the user, cutting off blood flow to fingertips when held under tension. The user is left with a waxy stickiness on their hands after flossing as they are handling the floss directly. Younger floss users have difficulty wrapping and manipulating the floss once wrapped around their fingers. Floss picks such as those made by Plackers, Dentek and Oral B are made from plastic and although they simplify the flossing procedure, they lack the desired level of intuitive two handed control. Attempts have also been made to make a disposable tooth-flossing device from wood to be more ecological. However, wood can snap and splinter. The present invention is directed toward overcoming one or more of the problems identified above.

SUMMARY OF THE INVENTION

The aforementioned deficiencies are addressed, and an advance is made in the art, by a disposable dental floss segment having rolled paper handle ends. The floss runs through the entire device. Between the two paper handles is an exposed section of floss. The two handles are separated by 19 mm of exposed floss. The rolled paper handles are similar to lollipop paper sticks or Q-tip cotton swab paper sticks.

In accordance with the first preferred embodiment of the present invention, each handle is formed from a sheet of paper that is tightly rolled. The paper can be printed on prior to rolling. This makes it possible to print comic book characters, graphics and popular fictional characters directly onto the handles, making the device more desirable for children. The paper sticks also serve as extensions, so the user does not have to stick their fingers all the way in their mouth to reach hard to reach spots. Rolled paper sticks have a small hole that run lengthwise through the center of the stick. For our purposes we will refer to this hole throughout as the 'roll hole'. The floss runs through this 'roll hole'. The floss is cut and heated at the ends to prevent the handles from sliding off when pulled taut by the user.

An object of the present invention is to provide a flossing device wherein the floss connects two separate handles through the center of the handles to provide best control and handling.

Another object of the present invention is to provide an inviting Pre-Cut, Ready-to-Grab dental flossing solution.

A further object of the present invention is to provide a floss segment with two cylindrical handle ends. By making the handles cylindrical there is no wrong way to pick them up or handle them. No fumbling for the correct grab orientation.

A further object of the present invention is to provide a flossing device that is disposable, easy to use and intuitive upon first sight. I wanted the solution to look like it's been around for years.

A further object of the present invention is to provide a disposable flossing device that does not employ glue or any additional plastic parts to anchor the floss ends.

Yet another object of the present invention is to provide a disposable dental flossing device that is easy to print full color comic book characters and graphics onto the entire length of it's handles.

A still further object of the present invention is to provide a disposable flossing device that can be used to help remove stains on teeth. Dentists have long recommended the use of broken Q-tips (cotton swab) paper sticks to rub on teeth to help remove stains.

BRIEF DESCRIPTION OF THE DRAWINGS

The various features, functions and advantages characterizing the invention will be better understood by reference to the detailed description which follows, taken in conjunction with the accompanying drawings, in which:

FIG. 3a is a top and side view of one rolled paper handle of the dental flossing device of FIG. 1.

FIG. 3b is a top and side view of an unrolled sheet of paper used to form one handle of the dental flossing device of FIG. 1.

FIG. 4a is a side view of one handle of a dental flossing device constructed in accordance with the present invention illustrating the cone effect that can be used to hide the fattened floss anchor and to make the floss section end of the handle convergent (pointy).

FIG. 4b is a side view of one handle of a dental flossing device constructed in accordance with the present invention illustrating the cone effect that can be used to hide the fattened floss anchor and to make the floss section end of the handle convergent. The floss is shown anchored at the inlet end and run thru the center 'roll hole' and out of the coned end to form the exposed floss section.

DETAILED DESCRIPTION OF THE INVENTION

Figure 1:
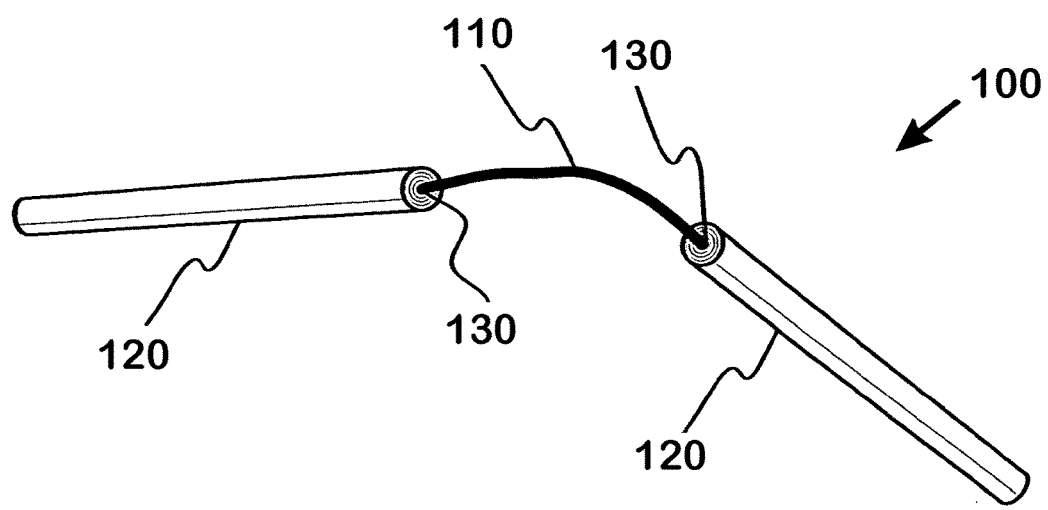
FIG. 1 is a perspective view of a dental flossing device constructed in accordance with the preferred embodiment of the present invention.

FIG. 1 illustrates a flossing device constructed in accordance with a first preferred embodiment of the present invention, shown generally at 100. Two tightly rolled paper handles 120 are threaded onto a mint waxed dental floss segment 110 that runs through the 'roll holes' 130 of both handles 120. The 'roll holes' 130 run through the entire length of each handle 120.

Figure 2A:
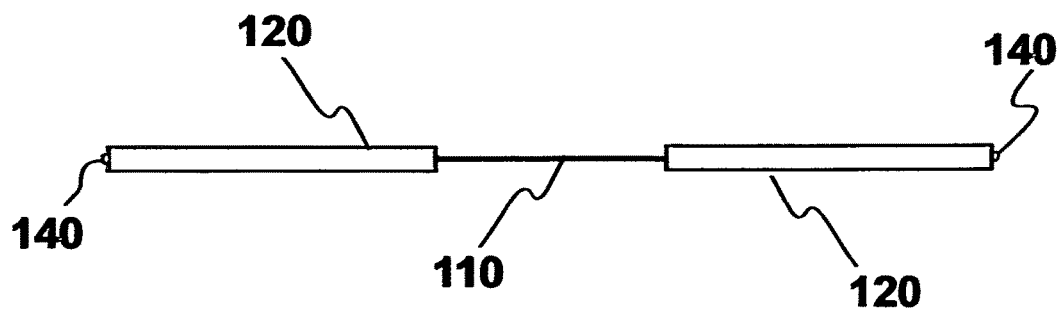
FIG. 2a is a plan view of the dental flossing device of FIG. 1.
Figure 2B:
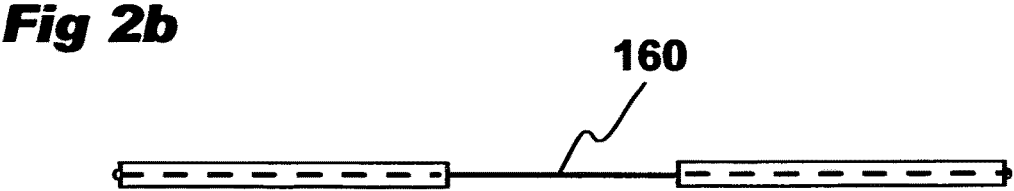
FIG. 2b is a plan view of the dental flossing device of FIG. 1 illustrating that the floss segment runs between and through the centers of the rolled paper handles at each end.
Figure 2C:
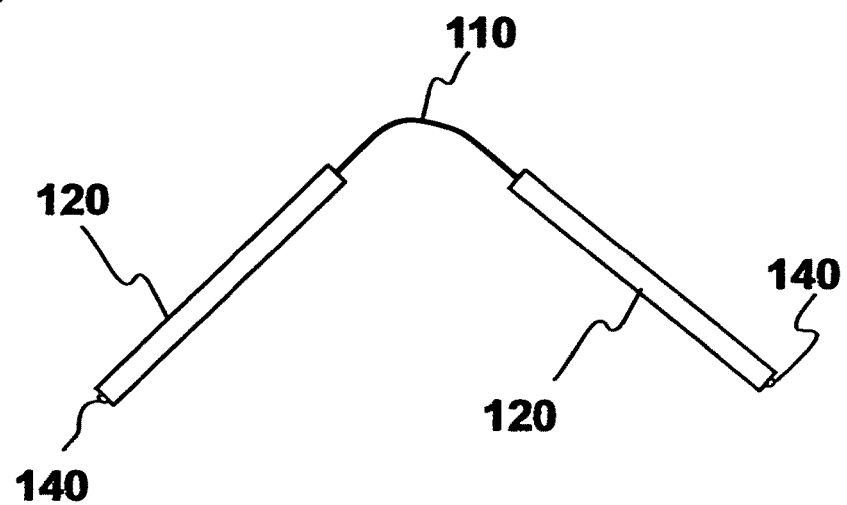
FIG. 2c is a plan view of the dental flossing device of FIG. 1 illustrating the loose exposed floss section.
Figure 5:
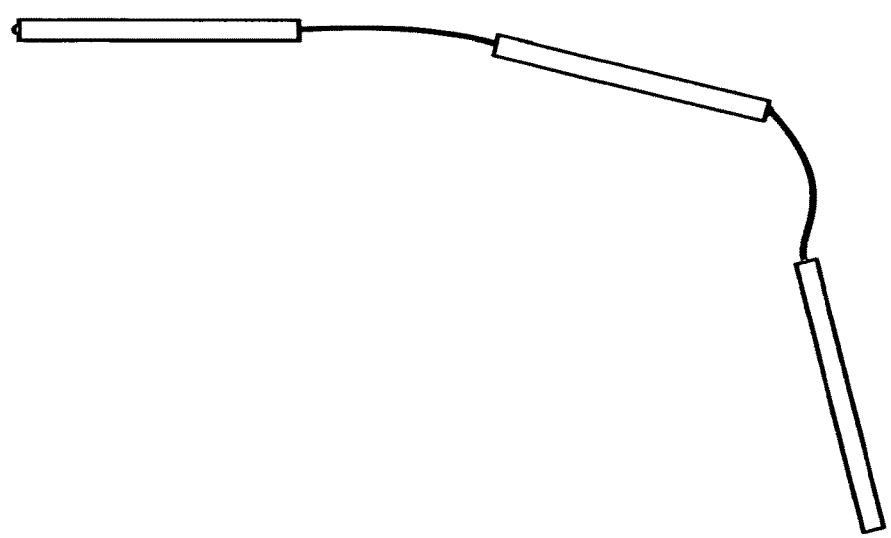
FIG. 5 is a plan view of a flossing device constructed in accordance with a second preferred embodiment of the present invention in which the device has more than two rolled paper handles. The middle handle(s) can be held in place with tied knots or double threading. A version with five handles and four exposed floss sections would provide one floss section per mouth quadrant.
Figure 6:
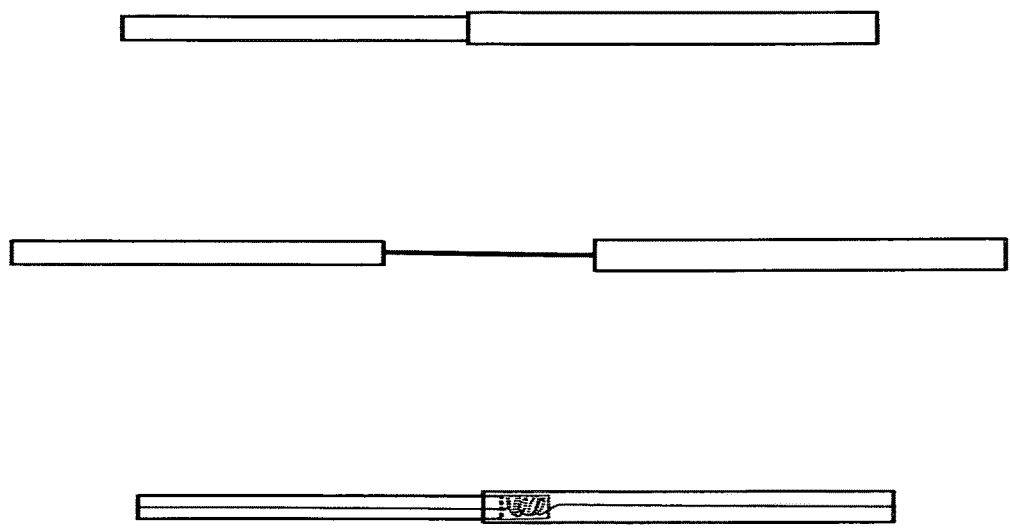
FIG. 6 is a plan view of a flossing device constructed in accordance with a third embodiment of the present invention in which the device has two rolled paper handles designed to fit together to form a single bar prior to use. The thinner handle nests in the tip of the larger handle and the floss is coiled in a small cavity between the two handles. When the user pulls the handles apart the coiled floss is exposed.

With reference to FIG. 2a and FIG. 2b one can see that the floss segment 110 runs through the 'roll holes' 130 of both handles. The floss segment 110 is cut and heated at each end 140. By heating the floss ends, the floss ends 140 fatten up and can no longer fit through the 'roll holes' 130, thereby anchoring the floss in the handles 120. The handles 120 will not slide off of the floss segment 110 when pulled taut by the user as the fattened ends 140 of the floss segment 110 are too large to fit through the 'roll holes' 130. The rolled paper handles 120 are identical. They each measure 32 mm in length and have a diameter of 2.5 mm. The diameter of the rolled paper handles 120 can vary between 2 mm and 10 mm. The length of the handles 120 can vary between 25 mm and 40 mm. If the handles 120 are made too long and too thin they begin to bend during use. If the handles are made too short they prove difficult to grab. The exposed floss section 160 separating the two handles 120 is 19 mm in length or in the range of 12 mm to 30 mm. With two handles 120 each measuring 32 mm in length and an exposed floss section 160 measuring 19 mm in length, the total length of the flossing device is 83 mm. That is 32 mm+32 mm+19 mm=83 mm.

The handles 120 are rolled with a very small amount of glue like Elmers multipurpose glue to stay rolled. A sealant coating may also be used on the rolled paper handles to protect them from getting wet and softening during use from the user's saliva, although this hasn't been an issue in testing. The diameter of each 'roll hole' 130 is 0.4 mm in diameter and can be made smaller or larger by changing the method by which the paper stick is rolled.

The rolled paper handles 120 can be threaded onto the floss 110 or they can be rolled directly onto the floss 110 and cut into sections and heated at each end to anchor. The heating and cutting operations can be a single operation with a hot knife.

A plastic material could also be used to form the two handles instead of rolled paper. In this case the plastic could be molded directly into the floss. The plastic would preferably be biodegradable. As an alternative to plastic, liquid wood can also be used to form the handles. Liquid wood is a composite of bio-based substances, such as wood fiber from sustainably-managed forests and lignin extracted from paper and candle wax during manufacturing processes.

Figure 7A:
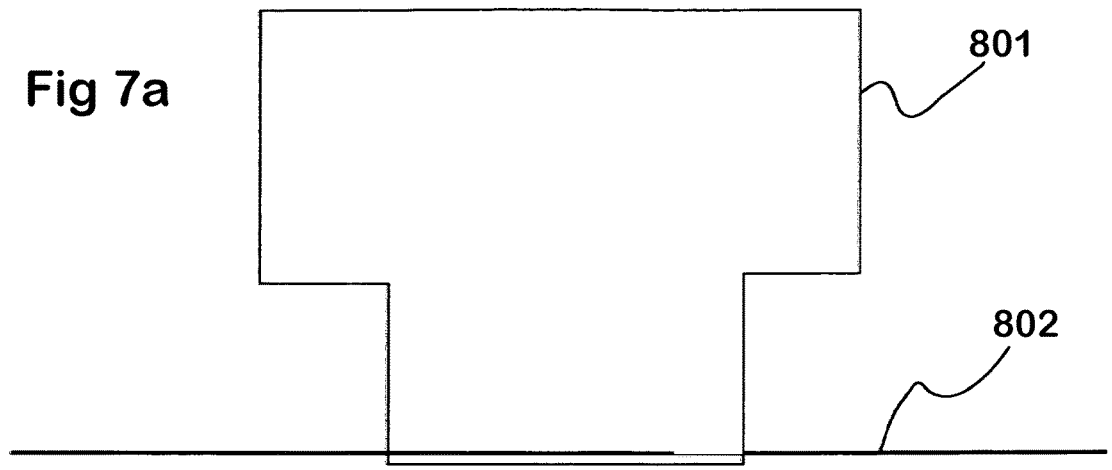
FIG. 7a is a plan view of a T shaped sheet of paper 801 before being rolled onto a a segment of floss 802.
Figure 7B:
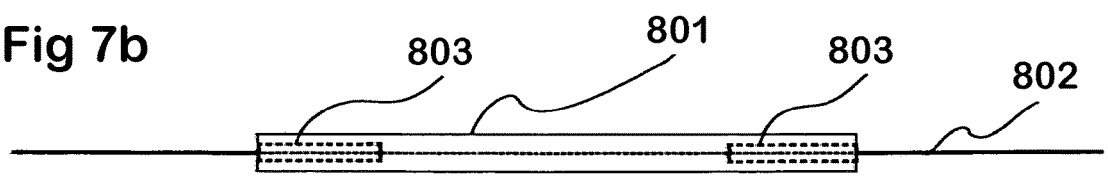
FIG. 7b is a side view of the T shaped sheet of paper 801 after it is rolled onto a segment of floss 802, illustrating the recesses on each end 803.
Figure 7C:
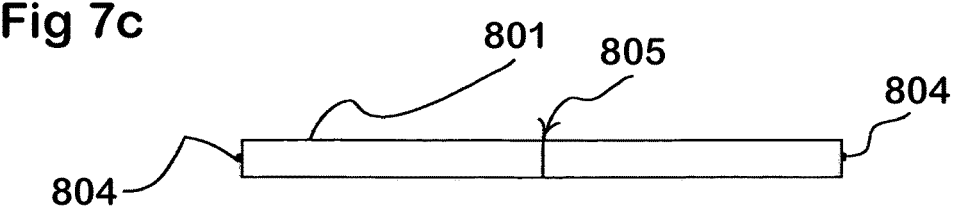
FIG. 7c is a side view of the Paper Stick with floss core formed from the T shaped sheet of paper 801.
Figure 8A:
FIG. 8a is a side view of the one-piece paper stick floss scored.
Figure 8B:
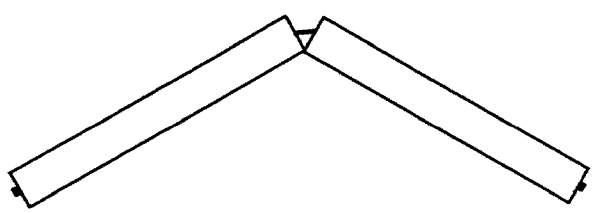
FIG. 8b is a side view of the one-piece paper stick floss broken in half.
Figure 8C:
FIG. 8c is a side view of the one-piece paper stick floss pulled apart to expose the floss segment.

With reference to FIGS. 7a, 7b and 7c, a method of high volume manufacture of a device constructed in accordance with the current invention that is delivered as a single piece is shown wherein a paper with smaller initial width 801 is rolled directly onto the floss string 802, creating a paper stick with cavities 803 in each end. The floss string 802 is then cut at each end and burned to create a swollen anchor 804 at each end. The middle of the paper stick is then lightly scored 805, so that the user can snap the paper stick in half and pull the two handles apart as demonstrated in FIGS. 8a, 8b and 8c. The swollen burnt floss ends move freely in the end cavities 803 and anchor where the cavities 803 stop. The Paper stick can be marked at its center with a printed break line to easily indicate where the user is to break the paper stick in half along with a printed logo and or graphic.

Should it prove too expensive to roll the paper directly onto the floss string, an alternative method is presented wherein the paper stick is rolled first and then the floss string is threaded or run through its center.

Should it prove too expensive to roll a paper stick with end cavities as demonstrated in FIGS. 7a, 7b and 7c, a standard stock paper stick may be used. The end cavities may then be drilled out using a double-sided pearl drilling machine or the like. The floss string would then be threaded through the center, the ends of the floss string cut and burned and the center of the stick scored.

With reference to FIG. 4a and FIG. 4b one can see that if the handles are rolled off center, a coned paper handle results. One end is concave and the other end is convex. This might be desirable to hide the fattened floss anchor ends and converge the exposed floss section ends of the handles 120.

The invention claimed is:

1. An apparatus for dental floss, comprising:
an elongate holding element having a length and a width, the length being longer than the width, the elongate element is formed by a rolled sheet of material having a bore with a first diameter extending therethrough substantially along a direction of the length, the bore having a first end and a second end, and the elongate holding element having a cylindrical outer surface with a diameter having a constant size along an entirety of the length of the elongate holding element; and
a floss string having two ends and extending through the bore, the ends of the floss string having a greater diameter than the first diameter of the bore,
the elongate holding element having a frangible section configured to be broken so that the elongate holding element can be separated into two parts at the frangible section and pulled apart along the floss string until the ends of the floss string respectively abut the first end and second end of the bore, whereby the floss string slides lengthwise through the bore of at least one of the two parts when the two parts are pulled apart,
wherein the elongate holding element includes a first side section extending lengthwise from the first end of the bore with a first counter bore having a second diameter, and a second side section extending lengthwise from the second end of the bore with a second counter bore having the second diameter, the first diameter being smaller than the second diameter.

2. The apparatus of claim 1 wherein the frangible section is a score in the elongate holding element.

3. The apparatus of claim 1, wherein the sheet of material is T-shaped in the unrolled state.

4. The apparatus of claim 1, wherein the sheet of material is paper.

5. The apparatus of claim 1, wherein the elongate holding element includes a plurality of frangible sections.

6. The apparatus of claim 1, wherein each of the two parts has a length in the range of 25 mm-40 mm, inclusive, and a diameter in the range of 2 mm-10 mm, inclusive.

7. The apparatus of claim 1, wherein the sheet has a sealant coating.

8. The apparatus of claim 1, wherein the elongate holding element has a graphic or character printed thereon.

9. The apparatus of claim 1, wherein a length of the floss string between the two parts of the elongate holding element after the two parts are separated is 12 mm-30 mm.

10. The apparatus of claim 1, wherein the ends of the floss string are heated to create the greater diameter.

\* \* \* \* \*